United States Patent [19]

Sato et al.

[11] Patent Number: 5,354,905

[45] Date of Patent: Oct. 11, 1994

[54] N-ALKOXYMETHYL BENZAMIDE DERIVATIVE AND MANUFACTURING METHOD THEREFOR, AND MANUFACTURING METHOD FOR BENZAMIDE DERIVATIVE USING THIS N-ALKOXYMETHYL BENZAMIDE DERIVATIVE

[75] Inventors: Yoshihiro Sato; Akihiro Koiso, both of Sakura; Tohru Asada, Shisui; Yasuhisa Miura, Sakura; Yasuo Kikuchi; Yasuaki Hariya, both of Nagano, all of Japan

[73] Assignee: Yashima Chemical Industry Co., Ltd., Tokyo, Japan

[21] Appl. No.: 138,423

[22] Filed: Oct. 20, 1993

[30] Foreign Application Priority Data

Oct. 23, 1992 [JP] Japan .................................. 4-286394
Oct. 23, 1992 [JP] Japan .................................. 4-286395

[51] Int. Cl.$^5$ .................. C09C 233/05; C09C 233/65
[52] U.S. Cl. ................................ 564/186; 548/237; 548/239
[58] Field of Search ................ 564/170, 176, 186; 548/237, 239; 514/374

[56] References Cited

FOREIGN PATENT DOCUMENTS 53-63337  6/1978  Japan .

OTHER PUBLICATIONS

Patent Abstracts of Japan, vol. 14, No. 280 (C-729) Jun. 18, 1990, Abstract JP-A-02 085 268 (Yashima Chem. Ind. Co. Ltd.) Mar. 26, 1990.
J. P. Lokensgard et al. "Synthesis of N-(a-Methoxyalkyl) Amides from Imidates", J. Org. Chem.; 85; vol. 50 (26), pp. 5609-5611, 1985.
Drach et al. Zh. Org. Khimii, vol. 14(3), 508-513, 1978.
Hoffmann et al., Chem. Ber. 109, 1759-1768, 1976.
Zinner et al., J. Prakt. Chemie, 323(6), 972-978, 1981.
Mikulasek et al., Chem. Zvesti, 33(4), 550-557, 1979.
Bohme et al., Arch. Pharm. 310(77), 242-248, 1977.
Balon et al., Zh. Org. Khimii, vol. 26, No. 9, 1892-1895, 1990.

*Primary Examiner*—Shailendra Kumer
*Attorney, Agent, or Firm*—Armstrong, Westerman, Hattori, McLeland & Naughton

[57] ABSTRACT

An N-alkoxymethyl benzamide derivative represented by Formula (I);

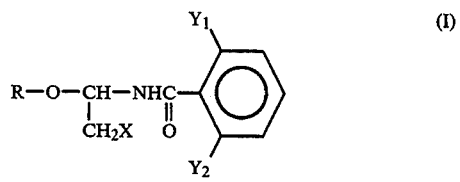

(In the formula, reference X indicates a halogen atom, references $Y_1$ and $Y_2$ indicate hydrogen atoms or halogen atoms, and may be identical or different, and reference R indicates a lower alkyl group.) and a manufacturing method for this N-alkoxymethyl benzamide derivative in which a substituted benzamide and an α-haloacetal are reacted. Furthermore, a manufacturing method for benzamide derivatives in which the N-alkoxymethyl benzamide derivative represented by Formula (I) above and benzene or a derivative thereof are reacted, and a benzamide derivative is produced. The N-alkoxymethyl benzamide derivative of the present invention is a novel compound, and possesses utility as an intermediate in the manufacturing of oxazoline derivatives which possess insecticidal and anti-mite activity, and as a starting material for the synthesis of various organic compounds and the like.

7 Claims, No Drawings

N-ALKOXYMETHYL BENZAMIDE DERIVATIVE AND MANUFACTURING METHOD THEREFOR, AND MANUFACTURING METHOD FOR BENZAMIDE DERIVATIVE USING THIS N-ALKOXYMETHYL BENZAMIDE DERIVATIVE

BACKGROUND OF THE INVENTION

The present invention relates to a novel N-alkoxymethyl benzamide derivative and a manufacturing method therefor. Furthermore, the present invention relates to a manufacturing method for benzamide derivative having applications as an intermediate in the synthesis of oxazoline derivative, utilizing this N-alkoxymethyl benzamide derivative.

It is known that oxazoline derivatives, which possess insecticidal and anti-mite activity, can be synthesized using the benzamide derivative shown in Formula (A) below as an intermediate.

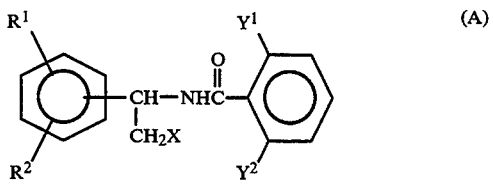

(In Formula (A), reference X indicates a halogen atom; references $Y_1$ and $Y_2$ indicate hydrogen atoms or halogen atoms which may be identical or different; and references $R^1$ and $R^2$ represent hydrogen atoms, halogen atoms, nitro groups, cyano groups, groups which may be non-periodically substituted selected from a group consisting of alkyl, alkenyl, alkynyl, aryl, and heteroaryl, or groups represented by $R^3O—$, $R^3S—$, $(R^3)_2N—$, $R^3CO—$, or $(R^3)_3Si—$. Herein, reference $R^3$ indicates a hydrogen atom, or a group, which may be nonperiodically substituted, selected from a group consisting of alkyl, alkenyl, alkynyl, aryl, heteroaryl, and alkyl amino carbonyl; $R^1$ and $R^2$ may be identical or different.)

As disclosed in Japanese Patent Application, First Publication No. 2-85268, this benzamide derivative is synthesized utilizing the amino ethanol derivative shown in Formula (B) below as a starting material.

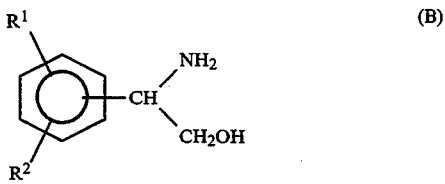

(In Formula (B), references $R^1$ and $R^2$ indicate hydrogen atoms alkyl groups, alkoxy groups, halogen atoms, trifluoro methyl groups, or trifluoro methoxyl groups, and $R^1$ and $R^2$ may be identical or different.)

However, when this conventional method was attempted by the present inventors, it was discovered that in order to synthesize the above-described amino ethanol derivative from easily obtainable materials, four processes were necessary. Furthermore, in order to synthesize the benzamide derivative shown in Formula (A) above from this amino ethanol derivative, two processes were necessary. That is to say, this conventional method involved a large number of processes, and the yield of the various processes was insufficient.

SUMMARY OF THE INVENTION

As a result of various researches into synthesis methods for the benzamide derivative described above, the present inventors have discovered that it is possible to synthesize this benzamide derivative easily and with a high yield by means of reacting the novel N-alkoxymethyl benzamide shown in Formula (I) below with benzene or a derivative thereof.

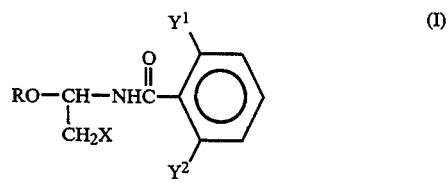

(In Formula (I), reference X indicates a halogen atom, references $Y_1$, and $Y_2$ indicate hydrogen atoms or halogen atoms that may be identical or different, and reference R indicates a lower alkyl group.)

The present inventors have found that this type of novel N-alkoxymethyl benzamide derivative can be synthesized in one process by means of the reaction of substituted benzamides with α-haloacetals, and that the compound thus obtained is stable. The reaction of, for example, substituted benzamides with halogenated acetaldehydes is known as a similar synthesis method; however, as the condensation product of individual molecules is unstable, it is difficult to isolate this product or to employ it as a reaction intermediate.

The present invention also provides a method for manufacturing the N-alkoxymethyl benzamide derivative shown in Formula (I) above, in which the substituted benzamide shown in Formula (II) below, and the α-haloacetal shown in Formula (III) below, are reacted.

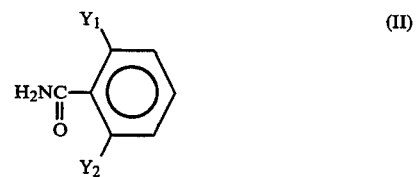

(In Formula (II), references $Y_1$ and $Y_2$ indicate hydrogen atoms or halogen atoms which may be identical or different.)

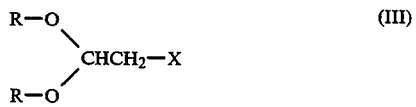

(In Formula (III), reference X indicates a halogen atom, while R indicates a lower alkyl group.)

Furthermore, the present invention provides a manufacturing method for benzamide derivatives, in which the benzamide derivative shown in Formula (V) below is produced by means of the reaction of the N-alkoxymethyl benzamide derivative shown in Formula (I) above with the benzene shown in Formula (IV) or a derivative thereof.

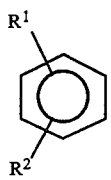
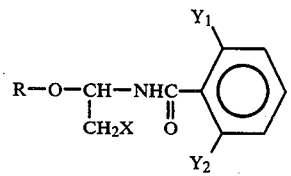

(In Formula (IV), references $R^1$ and $R^2$ represent hydrogen atoms, halogen atoms, nitro groups, cyano groups, groups which may be nonperiodically substituted selected from a group consisting of alkyl, alkenyl, alkynyl, aryl, and heteroaryl, or groups represented by $R^3O—$, $R^3S—$, $(R^3)_2N—$, $R^3CO—$, or $(R^3)_3Si—$; $R^1$ and $R^2$ may be identical or different. Herein, reference $R^3$ indicates a hydrogen atom, or a group, which may be nonperiodically substituted, selected from a group consisting of alkyl, alkenyl, alkynyl, aryl, heteroaryl, and alkyl amino carbonyl; $R^1$ and $R^2$ may be identical or different.)

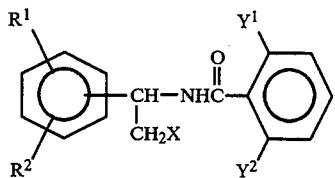

(In Formula (V), references X, $Y^1$, $Y^2$, $R^1$ and $R^2$ have meanings which are identical to those given above.)

The N-alkoxymethyl benzamide derivative of the present invention is a novel and stable compound, and it may be isolated and utilized as a reaction intermediate. This N-alkoxymethyl benzamide derivative is useful, in particular, as a starting material for benzamide derivatives which are intermediates used in the synthesis of oxazoline derivatives which possess insecticidal and anti-mite activity. Furthermore, the synthesis method of the N-alkoxymethyl benzamide derivative in accordance with the present invention comprises only a single process in which a substituted benzamide and an α-haloacetal are reacted.

Furthermore, the present invention discloses a manufacturing method for benzamide derivatives using this N-alkoxymethyl benzamide derivative. This method enables, in a simple manner, the synthesis of benzamide derivatives by means of the reaction of N-alkoxymethyl benzamide derivative with benzene or a derivative thereof. Accordingly, by means of utilizing this benzamide derivative, for example, as a intermediate in the synthesis of oxazoline derivatives, the number of processes involved in the synthesis thereof can be greatly reduced in comparison with the conventional methods.

DETAILED DESCRIPTION OF THE INVENTION

Hereinbelow, the present invention will be explained in detail.

The N-alkoxymethyl benzamide derivative of the present invention is represented by Formula (I) below.

(In Formula (I), reference X indicates a halogen atom, references $Y_1$ and $Y_2$ indicate hydrogen atoms or halogen atoms which may be identical or different; and while reference R indicates a lower alkyl group.)

Examples of the halogen atoms in the N-alkoxymethyl benzamide derivative of the present invention include, for example, fluorine atoms, chlorine atoms, bromine atoms, and iodine atoms. Furthermore, the lower alkyl group may have a straight chain or a branched chain form; examples thereof include, for example, methyl groups, butyl groups, and the like.

Furthermore, the present invention provides a manufacturing method for N-alkoxymethyl benzamide derivative in which the benzamide derivative represented by Formula (I) above is produced by means of the reaction of the substituted benzamide represented by Formula (II) below and the α-haloacetal represented by Formula (III) below.

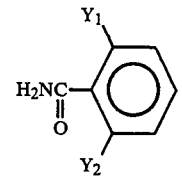

(In Formula (II), references $Y_1$ and $Y_2$ indicate hydrogen atoms or halogen atoms which may be identical or different.)

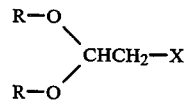

(In Formula (III), reference X indicates a halogen atom, while R indicates a lower alkyl group.)

In the present invention, examples of the substituted benzamide (Formula (II)) used as a reactant, include, for example, benzamide, 2-fluorobenzamide, 2-chlorobenzamide, 2-bromobenzamide, 2-iodobenzamide; 2,6-difluorobenzamide, 2,6-dichlorobenzamide, 2,6-dibromobenzamide, 2,6-diiodobenzamide; 2-fluoro-6-chlorobenzamide, 2-fluoro-6-bromobenzamide, 2-chloro-6-bromobenzamide, and the like; furthermore, examples of the α-haloacetal include, for example, chloroacetaldehyde dimethylacetal, chloroacetaldehyde diethylacetal, bromoacetaldehyde dimethylacetal, bromoacetaldehyde diethylacetal, and the like.

The reaction of a substituted benzamide and an α-haloacetal in the manufacturing method of the present invention can be conducted without the use of a catalyst; however, it is normally desirable that the reaction take place in the presence of an acid catalyst. No particular restriction is made with respect to these acid catalysts; however, examples thereof include, for example, inorganic acids such as sulfuric acid, hydrochloric acid, phosphoric acid, and the like, carboxylic acids such as acetic acid, benzoic acid, and the like, organic sulfonic acids, such as p-toluene sulfonic acid, methane sulfonic acid, and the like, Lewis acids such as aluminum chloride, boron fluoride, and the like, cation exchanging resins, and the like.

Furthermore, the above-described reaction does not particularly require a solvent, and can be conducted in the absence of a solvent; however, it is also possible to conduct the reaction utilizing a solvent. No particular restriction is made with respect to this solvent, insofar as it does not hinder the reaction and is capable of dissolving the starting materials to a certain extent; examples of such solvents include, for example, aromatic hydrocarbons such as benzene, toluene, and xylene; halogenated hydrocarbons such as methylene chloride and chloroform; esters such as ethyl acetate and propyl acetate; ethers such as tetrahydrofuran, diethyl ether, dioxan, and dimethoxy ethane; ketones such as acetone and methyl ethyl ketone; alcohols such as n-butanol; amides such as dimethyl formamide and dimethyl acetoamide; and sulfoxides such as dimethyl sulfoxide.

The reaction temperatures differ depending on the reactant compounds, and the type of catalyst and solvent used; however, the reaction temperature should be within a range of from −5° C. to 150° C., and preferably within a range of 50° C. to 100° C.

The reaction period varies depending on the reaction temperature, the reactant compounds, and the type of catalyst and solvent used; however, this period is normally within a range of from 30 minutes to several hours.

The reaction is normally conducted as a batch process; however, by using a solid acid such as an ion exchanging resin or the like, it is possible to conduct the reaction as a continuous process.

In the above-described reaction, with respect to one equivalent of the substituted benzamide described above, 1 to 10 equivalents of the α-haloacetal, and preferably 1.5 to 3 equivalents thereof, are normally used. However, in the case in which the reaction is conducted continuously while recovering excess α-haloacetal, the amount of α-haloacetal used is not necessarily so limited.

The amount of catalyst used is normally, with respect to one equivalent of substituted benzamide, within a range of 0.001 to 1 equivalent, and preferably within a range of 0.01 to 0.5 equivalents. However, in the case in which the reaction is conducted continuously, the amount of catalyst is not necessarily so limited.

After the reaction goes to completion, normal post-processing, for example, the washing and filtration of the reaction fluid in order to remove the catalyst, the removal by distillation of the excess α-haloacetal, and the like, is conducted, and when necessary, it is possible to conduct refining by means of operations such as chromatography, recrystallization, and the like.

Examples of the N-alkoxymethyl benzamide derivative of the present invention which is manufactured as described above, include, for example, the compounds listed below.

N-(1-methoxy-2-chloroethyl)-benzamide,
N-(1-methoxy-2-chloroethyl)-2-fluorobenzamide,
N-(1-methoxy-2-chloroethyl)-2-chlorobenzamide,
N-(1-methoxy-2-chloroethyl)-2-bromobenzamide,
N-(1-methoxy-2-chloroethyl)-2-iodobenzamide,
N-(1-methoxy-2-chloroethyl)-2,6-difluorobenzamide,
N-(1-methoxy-2-chloroethyl)-2,6-dichlorobenzamide,
N-(1-methoxy-2-chloroethyl)-2-fluoro-6-chlorobenzamide,
N-(1-ethoxy-2-chloroethyl)-2,6-difluorobenzamide,
N-(1-methoxy-2-bromoethyl)-2,6-difluorobenzamide, and the like.

Furthermore, the present invention provides a manufacturing method for benzamide derivatives in which the N-alkoxymethyl benzamide derivative shown in Formula (I) above is reacted with the benzene shown in Formula (IV) below or a derivative thereof, and the benzamide derivative shown in Formula (V) below is produced.

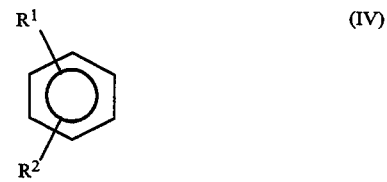

(In Formula (IV), references $R^1$ and $R^2$ indicate hydrogen atoms, halogen atoms, nitro groups, cyano groups, groups, which may be nonperiodically substituted, selected from a group consisting of alkyl, alkenyl, alkynyl, aryl, and heteroaryl, or groups represented by the formulas $R^3O-$, $R^3S-$, $(R^3)_2N-$, $R^3CO-$, or $(R^3)_3Si-$; $R^1$ and $R^2$ may be identical or different. Herein, $R^3$ represents a hydrogen atom or a group, which may be nonperiodically substituted, selected from a group consisting of alkyl, alkenyl, alkynyl, aryl, heteroaryl, and alkyl amino carbonyl.)

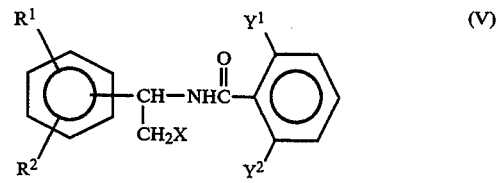

(In Formula (V), references X, $Y^1$, $Y^2$, $R^1$ and $R^2$ are defined as above.)

Examples of the group represented by references $R^1$ and $R^2$ in the benzene derivative shown in Formula (IV) include, for example, methyl group, ethyl group, propyl group, butyl group, pentyl group, hexyl group, heptyl group, octyl group, nonyl group, decyl group, ethenyl group, propenyl group, ethynyl group, propynyl group, chloromethyl group, hydroxymethyl group, acetyl oxymethyl group, trifluoromethyl group, methoxymethyl group, phenyl methyl group, isopropyl phenyl methyl group, methoxy phenyl methyl group, phenyl ethyl group, phenyl group, fluorophenyl group, methyl phenyl group, butyl phenyl group, methoxy phenyl group, trimethyl silylphenyl group, trifluoro methyl phenyl group, trifluoro methoxy phenyl group, pyridine group, methyl pyridine group, hydroxyl group, hydrothio group, amino group, acetyl group, benzoyl group, methoxyl group, butoxyl group, allyloxy group, geranyloxy group, propargyloxy group, phenoxy group, pyridyloxy group, methylthio group, trifluoromethyl phenyloxy group, trifluoro methoxy phenyloxy group, chlorophenyloxy group, nonylthio group, phenylthio group, dimethyl amino group, phenyl amino group, trimethyl silyl group, acetyloxy group, ethoxy carbonyl group, benzoyl amino group, methyl amino carbonyl amino group, dimethyl phenyl silyl group, and the like.

The reaction of the N-alkoxymethyl benzamide derivative and benzene or a derivative thereof in the manufacturing method in accordance with the present invention is shown in Reaction Formula (1) below.

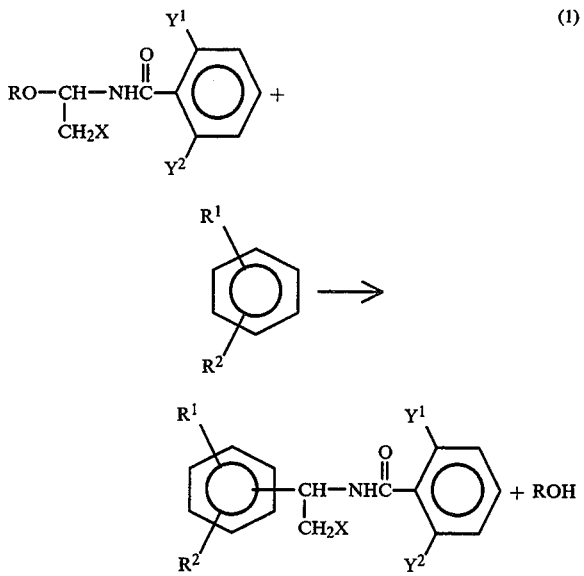

(In Formula (1), reference X indicates a halogen atom; references $Y_1$ and $Y_2$ indicate hydrogen atoms or halogen atoms which may be identical or different; and references $R^1$ and $R^2$ represent hydrogen atoms, halogen atoms, nitro groups, cyano groups, groups which may be non-periodically substituted selected from a group consisting of alkyl, alkenyl, alkynyl, aryl, and heteroaryl, or groups represented by $R^3O-$, $R^3S-$, $(R^3)_2N-$, $R^3CO-$, or $(R^3)_3Si-$. Herein, reference $R^3$ indicates a hydrogen atom, or a group, which may be nonperiodically substituted, selected from a group consisting of alkyl, alkenyl, alkynyl, aryl, heteroaryl, and alkyl amino carbonyl; $R^1$ and $R^2$ may be identical or different, while R indicates a lower alkyl group.)

The reaction described above can be carried out in the absence of a catalyst; however, normally, it is desirable that the reaction will be carried out in the presence of an acid catalyst. No particular limitation is made with respect to this acid catalyst; however, examples thereof include, for example, inorganic acids such as sulfuric acid, hydrochloric acid, nitric acid, phosphoric acid, perchloric acid and the like; carboxylic acids such as acetic acid, benzoic acid, and the like; organic sulfonic acids, such as p-toluene sulfonic acid, methane sulfonic acid, and the like; Lewis acids such as aluminum chloride, titanium tetrachloride, boron fluoride, phosphorus oxychloride, and the like; cation exchanging resins, and the like.

A solvent is not particularly required in the present reaction, and the reaction can be accomplished without the use of a solvent; however, it is also possible to use a solvent in the reaction. Insofar as the solvent does not hinder the reaction and is capable of dissolving the starting materials to a certain extent, no particular restriction is made with respect to this solvent; examples thereof include, for example, aliphatic hydrocarbons such as n-hexane, ligroin, petroleum ether, and the like; aromatic hydrocarbons such as benzene, toluene, xylene, and the like, halogenated hydrocarbons such as methylene chloride, chloroform, and the like; esters such as ethyl acetate, propyl acetate, and the like; ethers such as diethyl ether, tetrahydrofuran, dioxan, dimethoxy ethane, and the like; ketones such as acetone and methyl ethyl ketone, and the like; alcohols such as methanol, n-butanol, and the like; amides such as dimethyl formamide, dimethyl acetoamide, and the like; and sulfoxides such as dimethyl sulfoxide, and the like.

The reaction temperatures differ depending on the reactant compounds, and the type of catalyst and solvent used; however, this temperature is normally within a range of $-20°$ C. to $200°$ C., and preferably between a range of $-10°$ C. to $70°$ C.

The reaction period varies based on the reaction temperature, the reactant compounds, and the type of catalyst and solvent used; however, this period is normally within a range of 30 minutes to 20 hours, and is preferably within a range of 1 hour to 6 hours.

The catalyst is normally present within a range of 0.001 to 10 equivalents per one equivalent of N-alkoxymethyl benzamide derivative, and is preferably within a range of 0.01 to 3 equivalents.

In the manufacturing method in accordance with the present invention, the benzene or derivative thereof is normally present in an amount within a range of 0.8 to 5 moles, and preferably within a range of 1 to 2 moles with respect to 1 mole of N-alkoxymethyl benzamide derivative.

The reaction is normally performed as a batch process; however, it may also be performed as a continuous process.

The benzamide derivative which was synthesized can be refined by commonly employed processes such as, for example, filtration, extraction, distillation, column chromatography, or the like.

Examples of the benzene derivative shown in Formula (IV), include: fluorobenzene, chlorobenzene, bromobenzene, iodobenzene, cyclohexyl benzene, nitrobenzene, benzonitrile, toluene, ethyl benzene, n-octyl benzene, styrene, allyl benzenes phenyl acetylene, biphenyl, 4-phenyl pyridine, benzyl chloride, benzyl alcohol, benzyl acetate, $\alpha,\alpha,\alpha$-trifluoro toluene, benzylmethyl ether, diphenyl methane, 4-isopropyl diphenyl methane, 4-methoxy diphenyl methane, bibenzyl, 2-fluoro biphenyl, 3-phenyl toluene, 2-methoxy biphenyl, 4-trimethyl silyl biphenyl, 3-methyl-2-phenyl pyridine, phenol, thiophenol, aniline, acetophenone, benzophenone, anisole, butyl phenyl ether, allyl phenyl ether, propynyl phenyl ether, diphenyl ether, phenyl pyridyl ether, thiophenol, thioanisole, phenyl sulfide, N,N-dimethyl aniline, diphenyl amine, phenyl trimethyl silane, phenyl acetate, ethyl benzoate, benzanilide, 1-methyl-3-phenyl urea, m-difluorobenzene, p-dichlorobenzene, 3-bromochlorobenzene, 1-chloro-2-nitrobenzene, 3-chloro toluene, 2-bromo anisole, 4,4'-difluoro biphenyl, 3-methoxy-4'-n-propyl biphenyl, 3-fluoro-4'-t-butyl diphenyl methane, 2-chloro-4-trifluoromethyl diphenyl ether, 1-chloro-3-trifluoromethoxy diphenyl ether, dimethyl diphenyl silane, and the like.

Examples of the compound which is shown in Formula (V) above and which is synthesized by means of the manufacturing method in accordance with the present invention, include, for example, the compounds shown in Tables 1 and 2 below.

The substitution positions of $R^1$ and $R^2$ may be any of the ortho, meta, or para positions.

TABLE 1

| Compound | R¹ | R² | X | Y¹ | Y² |
|---|---|---|---|---|---|
| 1 | CH₃O | CH₃O | Cl | H | H |
| 2 | OH | t-C₄H₉ | Cl | Cl | Cl |
| 3 | C₂H₅O | t-C₄H₉ | Cl | F | F |
| 4 | CH₃ | H | Cl | F | H |
| 5 | n-C₈H₁₇ | H | Cl | Br | H |
| 6 | CH₃O | CF₃ | Cl | I | H |
| 7 | 4-CF₃O—C₆H₄ | F | Cl | Cl | Cl |
| 8 | CH₃COO | t-C₄H₉ | Cl | F | F |
| 9 | CH₃NHCONH | H | Cl | F | F |
| 10 | C₆H₅CONH | H | Cl | F | F |
| 11 | n-C₈H₁₇ | H | Cl | F | F |
| 12 | 4-CF₃O—C₆H₄ | H | Cl | F | F |
| 13 | 4-CF₃O—C₆H₄ | H | Cl | F | Cl |
| 14 | Cl | H | Cl | F | H |
| 15 | CH₃O | H | Cl | Cl | H |
| 16 | CN | H | Cl | F | Cl |
| 17 | CH₃CO | t-C₄H₉ | Cl | F | Cl |

TABLE 2

| Compound | R¹ | R² | X | Y¹ | Y² |
|---|---|---|---|---|---|
| 18 | CH₃O | NO₂ | Cl | Cl | Cl |
| 19 | CF₃—C₆H₄ | H | Cl | Cl | Cl |
| 20 | (4-Cl—C₆H₄)O | H | Cl | Br | Br |
| 21 | C₂H₅OCO | C₂H₅O | Cl | F | F |
| 22 | n-C₉H₁₉S | H | Cl | H | H |
| 23 | 4-[(CH₃)₃Si]C₆H₄ | H | Cl | F | H |
| 24 | (CH₃)₃Si | H | Cl | F | F |
| 25 | C₆H₅(CH₃)₂Si | H | Cl | F | F |
| 26 | (4-ClC₆H₄)O | Cl | Cl | Cl | H |
| 27 | Geranyloxy | H | Cl | F | F |
| 28 | Propargyloxy | H | Cl | F | F |
| 29 | C₅H₄N | H | Cl | F | F |
| 30 | Cl | Cl | Br | Cl | Cl |
| 31 | CH₃O | F | Br | F | F |
| 32 | Cl | iso-C₃H₇ | Cl | H | H |
| 33 | Cl | n-C₅H₁₁ | Cl | F | F |
| 34 | F | n-C₅H₁₁ | Cl | F | F |
| 35 | Cl | n-C₇H₁₅ | Cl | F | F |
| 36 | F | n-C₉H₁₉ | Cl | F | F |

The benzamide derivative obtained by means of the manufacturing method in accordance with the present invention can be used to obtain, by means of the reactions shown in Reaction Formula (2) below, an oxazoline derivative possessing insecticidal and anti-mite activity.

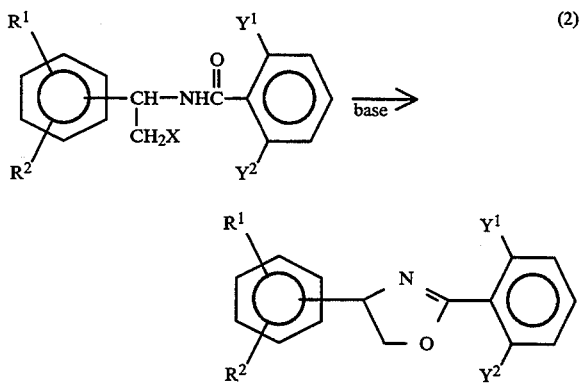

(In Formula (2), reference X indicates a halogen atom; references $Y_1$ and $Y_2$ indicate hydrogen atoms or halogen atoms which may be identical or different; and references $R^1$ and $R^2$ represent hydrogen atoms, halogen atoms, nitro groups, cyano groups, groups which may be non-periodically substituted selected from a group consisting of alkyl, alkenyl, alkynyl, aryl, and heteroaryl, or groups represented by $R^3O-$, $R^3S-$, $(R^3)_2N-$, $R^3CO-$, or $(R^3)_3Si-$. Herein, reference $R^3$ indicates a hydrogen atom, or a group, which may be nonperiodically substituted, selected from a group consisting of alkyl, alkenyl, alkynyl, aryl, heteroaryl, and alkyl amino carbonyl; $R^1$ and $R^2$ may be identical or different.)

EXPERIMENTAL EXAMPLES

Next, the present invention will be explained based on experimental examples; however, the present invention is not limited to the benzamide derivatives and the manufacturing methods therefor which are described hereinbelow.

Example 1

Synthesis of N-(1-methoxy-2-chloroethyl)-benzamide (1)

12.1 g of benzamide and 14.3 g of chloroacetaldehyde dimethyl acetal were agitated while being cooled in an ice bath, and into this, 7 ml of concentrated sulfuric acid was dripped over a period of 1 hour. After agitating this for 2 hours at room temperature, 200 ml of water was added to the reaction fluid, and this was extracted in 300 ml of chloroform. The extracted layer was washed twice with 100 ml of water, and the chloroform and excess chloroacetaldehyde dimethyl acetal were removed by distillation under reduced pressure, and 15.0 g of compound (1) was obtained.

melting point: 76.9°–77.7° C. ¹H-NMR (60 MHz, CDCl₃, TMS) δ: 3.45 (s, 3H), 3.72 (d, 2H, J=4.0 Hz), 5.40–5.75 (m, 1H), 6.60–7.15 (br, 1H), 7.30–7.60 (m, 3H), 7.70–7.95 (m, 2H)

Example 2

Synthesis of N-(1-methoxy-2-chloroethyl)-benzamide (2)

9.6 g of benzamide and 49.8 g of chloroacetaldehyde dimethyl acetal, and an amount of strongly acidic ion exchanging resin having an exchange capacity corresponding to the benzamide were agitated for 3 hours at a temperature of 60° C. The reaction fluid was cooled to 40° C., and 30 ml of dichloromethane was added thereto. The ion exchanging resin was removed by filtration under reduced pressure, and the dichloromethane and excess chloroacetaldehyde dimethyl acetal were removed from the filtrate by vacuum distillation, 100 ml of hexane was added thereto and crystals were precipitated, and these were then filtered and desiccated to obtain 7.0 g of compound (1).

Example 3

Synthesis of N-(1-methoxy-2-chloroethyl)-2-fluorobenzamide

Utilizing a manufacturing method identical to that of preferred embodiment 2, 8.0 g of compound (2) was obtained from 10.0 g of 2-fluorobenzamide and 44.8 g of chloroacetaldehyde dimethyl acetal.

melting point: 49.7°–50.8° C. ¹H-NMR (60 MHz, CDCl₃, TMS) δ: 3.50 (s, 3H), 3.73 (d, 2H, J=4.0 Hz), 5.50–5.85 (m, 1H), 6.95–7.70 (m, 4H), 7.90–8.29 (m, 1H)

Example 4

Synthesis of N-(1-methoxy-2-chloroethyl)-2-chlorobenzamide

Utilizing a manufacturing method identical to that of preferred embodiment 2, 9.6 g of compound (3) was obtained from 7.8 g of 2-chlorobenzamide and 31.1 g of chloroacetaldehyde dimethyl acetal.

melting point: 105.9°–106.5° C. $^1$H-NMR (60 MHz, CDCl$_3$, TMS) δ: 3.50 (s, 3H), 3.70 (d, 2H, J=5.8 Hz), 5.52–5.63 (m, 1H), 7.25–7.70 (m, 4H), 8.00–8.45 (br, 1H)

Example 5

Synthesis of N-(1-methoxy-2-chloroethyl)-2-bromobenzamide

Utilizing a manufacturing method identical to that of preferred embodiment 2, 11.1 g of compound (4) was obtained from 10.3 g of 2-bromobenzamide and 32.1 g of chloroacetaldehyde dimethyl acetal.

melting point: 121.0°–121.7° C. $^1$H-NMR (60 MHz, CDCl$_3$, TMS) δ: 3.52 (s, 3H), 3.69 (d, 2H, J=5.8 Hz), 5.20–5.62 (m, 1H), 7.15–7.75 (m, 4H), 8.20–8.65 (br, 1H)

Example 6

Synthesis of N-(1-methoxy-2-chloroethyl)-2-iodobenzamide

Utilizing a manufacturing method identical to that of preferred embodiment 2, 5.8 g of compound (5) was obtained from 6.0 g of 2-iodobenzamide and 15.1 g of chloroacetaldehyde dimethyl acetal.

melting point: 113.4°–114.0° C. $^1$H-NMR (60 MHz, CDCl$_3$, TMS) δ: 3.65 (s, 3H), 3.75 (d, 2H, J=4.0 Hz), 5.38–5.70 (m, 1H), 6.32–6.70 (br, 1H), 6.90–7.50 (m, 3H), 7.78–7.98 (m, 1H)

Example 7

Synthesis of N-(1-methoxy-2-chloroethyl)-2,6-difluorobenzamide

Utilizing a manufacturing method identical to that of preferred embodiment 2, 19.6 g of compound (6) was obtained from 15.7 g of 2,6-difluorobenzamide and 62.3 g of chloroacetaldehyde dimethyl acetal.

melting point: 90.4°–91.6° C. $^1$H-NMR (60 MHz, CDCl$_3$, TMS) δ: 3.45 (s, 3H), 3.69 (d, 2H, J=4.0 Hz), 5.35–5.71 (m, 1H), 6.48–6.80 (br, 1H), 6.80–7.60 (m, 3H)

Example 8

Synthesis of N-(1-methoxy-2-chloroethyl)-2,6-dichlorobenzamide

Utilizing a manufacturing method identical to that of preferred embodiment 2, 9.0 g of compound (7) was obtained from 10.0 g of 2,6-dichlorobenzamide and 32.8 g of chloroacetaldehyde dimethyl acetal.

melting point: 159.3°–160.2° C. $^1$H-NMR (60 MHz, CDCl$_3$, TMS) δ: 3.53 (s, 3H), 3.66 (d, 2H, J=5.8 Hz), 5.20–5.60 (m, 1H), 7.35 (s, 3H), 8.66–9.00 (br, 1H)

Example 9

Synthesis of N-(1-methoxy-2-chloroethyl)-2-fluoro-6-chlorobenzamide

Utilizing a manufacturing method identical to that of preferred embodiment 2, 7.3 g of compound (8) was obtained from 6.5 g of 2-fluoro-6-chlorobenzamide and 23.0 g of chloroacetaldehyde dimethyl acetal.

melting point: 134.8°–135.5° C. $^1$H-NMR (60 MHz, CDCl$_3$, TMS) δ: 3.50 (s, 3H), 3.65 (d, 2H, J=5.8 Hz), 5.20–5.58 (m, 1H), 6.85–7.50 (m, 3H), 8.55–9.00 (br, 1H)

Example 10

Synthesis of N-(1-ethoxy-2-chloroethyl)-2,6-difluorobenzamide

Utilizing a manufacturing method identical to that of preferred embodiment 2, 10.4 g of compound (9) was obtained from 8.6 g of 2,6-difluorobenzamide and 25.0 g of chloroacetaldehyde diethyl acetal.

melting point: 71.8°–72.6° C. $^1$H-NMR (60 MHz, CDCl$_3$, TMS) δ: 1.25 (t, 3H, J=7 Hz), 3.45–3.90 (m, 4H), 5.45–5.80 (m, 1H), 6.47–7.58 (m, 4H)

Example 11

Synthesis of N-(1-methoxy-2-bromoethyl)-2,6-difluorobenzamide

Utilizing a manufacturing method identical to that of preferred embodiment 2, 10.2 g of compound (10) was obtained from 7.7 g of 2,6-difluorobenzamide and 25.0 g of bromoacetaldehyde dimethyl acetal.

melting point: 99.3°–100.7° C. $^1$H-NMR (60 MHz, CDCl$_3$, TMS) δ: 3.50 (s, 3H), 3.55 (d, 2H, J=4 Hz), 5.32–5.70 (m, 1H), 6.40–7.60 (m, 4H)

Example 12

Continuous manufacturing method 85 g of a strongly acidic ion exchanging resin having an exchange capacity of 4 meq/g was placed in a glass column having an inner diameter of 35 mm, and this was heated to a temperature of 70° C. in a hot bath. To this was supplied a solution of 1 part per weight of benzamide dissolved in 10 parts per weight of chloroacetaldehyde dimethyl acetal at a rate of 230 g per hour via a volumetric pump. 230 g of the reaction fluid discharged from the column was concentrated by distillation chloroacetaldehyde dimethyl acetal under reduced pressure so as to reach an amount of 130 g. Next, 100 ml of n-hexane was added thereto, the precipitated crystals were filtered out, and thus 33.7 g of N-(1-methoxy-2-chloroethyl)-benzamide [Compound (1)] was obtained. With respect to the expended benzamide, the yield was 91%.

Next, the manufacturing method for benzamide derivatives utilizing the N-alkoxymethyl benzamide derivative of the present invention will be explained by means of preferred embodiments; however, the present invention is not limited to the manufacturing methods for benzamide derivatives shown hereinbelow.

Example 13

Synthesis of N-[2-chloro-1-(2,5-dimethoxy) phenyl ethyl] benzamide 2.1 g of N-(1-methoxy-2-chloroethyl) benzamide and 2.8 g of 1,4-dimethoxy benzene were dissolved in 20 ml of acetic acid, and 0.1 g of concentrated sulfuric acid was added thereto while cooling in an ice bath. After reaction was allowed to occur for a period of 5 hours at room temperature, 50 ml of water was added to the reaction fluid, and extraction was conducted by means of 50 ml of dichloromethane. The extracted layer was washed twice with 50 ml of water, was desiccated in anhydrous sodium sulfate, the dichloromethane was removed by distillation, the reaction fluid was concentrated, the precipitated target compound was obtained by filtration, desiccated, and 2.6 g of N-[2-chloro-1-(2,5-dimethoxy) phenyl ethyl] benzamide was thus obtained.

With respect to the N-(1-methoxy-2-chloroethyl) benzamide, the yield was 81%.

Example 14

Synthesis of 2,6-dichloro-N-[2-chloro-1-(2-hydroxy-4-t-butyl) phenyl ethyl] benzamide 2.8 g of 2,6-dichloro-N-(1-methoxy-2-chloroethyl) benzamide was agitated with 3.0 g of m-t-butyl phenol at a temperature of 70° C., and 1.1 g of phosphorus oxychloride was dripped thereinto. After agitation was continued for a period of 3 hours at a temperature within a range of 70° to 80° C., the reaction fluid was cooled to a temperature of 50° C., 5 ml of n-hexane was added thereto, and this was stored overnight while slowly adding 5 ml of water. The precipitated crystals were obtained by filtration, these were washed with water and n-hexane, and desiccated, and thus 3.1 g of 2,6-dichloro-N-[2-chloro-1-(2-hydroxy-4-t-butyl) phenyl ethyl] benzamide was obtained. With respect to the 2,6-dichloro-N-(1-methoxy-2-chloroethyl) benzamide, the yield was 78%.

Example 15

Synthesis of 2,6-difluoro-N-[2-chloro-1-(2-ethoxy-5-t-butyl) phenyl ethyl] benzamide 2.6 g of anhydrous aluminum chloride was dissolved in 10 ml of dichloromethane, and this was agitated while being cooled. Into this was dripped, over a period of 10 minutes, a solution of 2.6 g of 2,6-difluoro-N-(1-ethoxy-2-chloroethyl) benzamide and 3.6 g of 4-t-butyl phenetole in 10 ml of dichloromethane. Next, the reaction fluid was slowly heated, and after conducting refluxing for a period of 2 hours, this was added to ice water. The dichloromethane layer was washed in the water, and after the removal of the dichloromethane, concentration was carried out and the precipitated crystals were obtained by filtration, and desiccated, and thus 3.5 g of 2,6-difluoro-N-[2-chloro-1-(2-ethoxy-5-t-butyl) phenyl ethyl] benzamide was obtained. With respect to the 2,6-difluoro-N-(1-ethoxy-2-chloroethyl) benzamide, the yield was 86%.

Examples 16–49

Using, in Preferred Embodiment 16, the manufacturing method shown in Preferred Embodiment 13, using, in Preferred Embodiments 17–25, the manufacturing method shown in Preferred Embodiment 14, and using, in Preferred Embodiments 26–49, the manufacturing method shown in Preferred Embodiment 15, the compounds shown in Tables 3 and 4 below were synthesized. The yields are shown in all cases as a molar yield with respect to the N-alkoxymethyl benzamide derivative.

TABLE 3

| Embodiment | Compounds of Formula (IV) $R^1$ | $R^2$ | Compounds of Formula (I) R | X | $Y^1$ | $Y^2$ | Catalyst | Yield (%) |
|---|---|---|---|---|---|---|---|---|
| 16 | $CH_3$ | H | $CH_3$ | Cl | F | H | $H_2SO_4$ | 90 |
| 17 | n-$C_8H_{17}$ | H | $CH_3$ | Cl | Br | H | $POCl_3$ | 74 |
| 18 | 1-$CH_3O$ | 3-$CF_3$ | $CH_3$ | Cl | I | H | $POCl_3$ | 71 |
| 19 | 1-(4-$CF_3O$)$C_6H_4$ | 3-F | $CH_3$ | Cl | Cl | Cl | $POCl_3$ | 68 |
| 20 | 1-$CH_3COO$ | 3-t-$C_4H_9$ | $CH_3$ | Cl | F | F | $POCl_3$ | 65 |
| 21 | $CH_3NHCONH$ | H | $CH_3$ | Cl | F | F | $POCl_3$ | 51 |
| 22 | $C_6H_5CONH$ | H | $CH_3$ | Cl | F | F | $POCl_3$ | 57 |
| 23 | n-$C_8H_{17}$ | H | $CH_3$ | Cl | F | F | $POCl_3$ | 73 |
| 24 | 4-$CF_3O$-$C_6H_4$ | H | $CH_3$ | Cl | F | F | $POCl_3$ | 71 |
| 25 | 4-$CF_3O$-$C_6H_4$ | H | $CH_3$ | Cl | F | Cl | $POCl_3$ | 69 |
| 26 | Cl | H | $CH_3$ | Cl | F | H | $AlCl_3$ | 97 |
| 27 | $CH_3O$ | H | $CH_3$ | Cl | Cl | H | $TiCl_4$ | 98 |
| 28 | CN | H | $CH_3$ | Cl | F | Cl | $AlCl_3$ | 63 |
| 29 | 1-$CH_3CO$ | 3-t-$C_4H_9$ | $CH_3$ | Cl | F | Cl | $AlCl_3$ | 55 |
| 30 | 1-$CH_3O$ | 3-$NO_2$ | $CH_3$ | Cl | Cl | Cl | $AlCl_3$ | 59 |
| 31 | 4-$CF_3$-$C_6H_4$ | H | $CH_3$ | Cl | Cl | Cl | $BF_3Et_2O$ | 95 |
| 32 | (4-Cl-$C_6H_4$)O | H | $CH_3$ | Cl | Br | Br | $AlCl_3$ | 88 |

TABLE 4

| Embodiment | Compounds of Formula (IV) $R^1$ | $R^2$ | Compounds of Formula (I) R | X | $Y^1$ | $Y^2$ | Catalyst | Yield (%) |
|---|---|---|---|---|---|---|---|---|
| 33 | $C_2H_5OCO$ | $C_2H_5O$ | $CH_3$ | Cl | F | F | $AlCl_3$ | 61 |
| 34 | n-$C_9H_{19}S$ | H | $C_2H_5$ | Cl | H | H | $AlCl_3$ | 93 |
| 35 | 4[($CH_3$)$_3$Si]$C_6H_4$ | H | $CH_3$ | Cl | F | H | $AlCl_3$ | 76 |
| 36 | ($CH_3$)$_3$Si | H | $CH_3$ | Cl | F | F | $TiCl_4$ | 83 |
| 37 | $C_6H_5(CH_3)_2Si$ | H | $CH_3$ | Cl | F | F | $AlCl_3$ | 87 |
| 38 | 1-(4-$ClC_6H_4$)O | 2-Cl | $CH_3$ | Cl | Cl | H | $AlCl_3$ | 71 |
| 39 | Geranyloxy | H | $CH_3$ | Cl | F | F | $AlCl_3$ | 55 |
| 40 | Propargyloxy | H | $CH_3$ | Cl | F | F | $AlCl_3$ | 52 |
| 41 | 2-$C_5H_4N$ | H | $CH_3$ | Cl | F | F | $AlCl_3$ | 62 |
| 42 | 1-Cl | 3-Cl | $CH_3$ | Br | Cl | Cl | $AlCl_3$ | 89 |
| 43 | 1-$CH_3O$ | 3-F | $CH_3$ | Br | F | F | $AlCl_3$ | 91 |
| 44 | 1-Cl | 2-iso-$C_3H_7$ | $CH_3$ | Cl | H | H | $TiCl_4$ | 87 |
| 45 | 1-Cl | 3-n-$C_5H_{11}$ | $CH_3$ | Cl | F | F | $TiCl_4$ | 73 |
| 46 | 1-F | 3-n-$C_5H_{11}$ | $CH_3$ | Cl | F | F | $TiCl_4$ | 78 |
| 47 | 1-Cl | 3-n-$C_7H_{15}$ | $CH_3$ | Cl | F | F | $TiCl_4$ | 76 |
| 48 | 1-F | 3-n-$C_9H_{19}$ | $CH_3$ | Cl | F | F | $TiCl_4$ | 80 |
| 49 | 1-$C_2H_5O$ | 3-t-$C_4H_9$ | $CH_3$ | Cl | F | F | $AlCl_3$ | 75 |

What is claimed is:

1. A manufacturing method for N-alkoxymethyl benzamide derivatives depicted in Formula (I), wherein a substituted benzamide represented by Formula (II) below and an α-haloacetal represented by Formula (III) below are reacted;

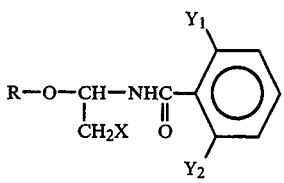 (I)

wherein, X indicates a halogen atom, $Y_1$ and $Y_2$ indicate hydrogen atoms or halogen atoms that are identical or different, and R indicates a lower alkyl group;

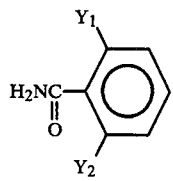 (II)

wherein, $Y_1$ and $Y_2$ represent hydrogen atoms or halogen atoms that are identical or different;

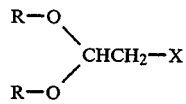 (III)

wherein, reference X indicates a halogen atom, and reference R indicates a lower alkyl group.

2. A manufacturing method for N-alkoxymethyl benzamide derivatives in accordance with claim 1, comprising a reaction process, wherein said substituted benzamide and said α-haloacetal are mixed and reacted, and a separation process, wherein, after the completion of said reaction process, from this reaction mixture, said N-alkoxymethyl benzamide derivative is separated.

3. A manufacturing method for N-alkoxymethyl benzamide derivatives in accordance with claim 2, wherein, in said reaction process, said substituted benzamide and said α-haloacetal are reacted in the presence of an acid catalyst.

4. A manufacturing method for N-alkoxymethyl benzamide derivatives in accordance with any one of claims 2 or 3, wherein, in said reaction process, with respect to one equivalent of said substituted benzamide, from 1 to 10 equivalents of said α-haloacetal are mixed.

5. A manufacturing method for N-alkoxymethyl benzamide derivatives in accordance with claim 3, wherein said acid catalyst is present in an amount of from 0,001 to 1 equivalent with respect to one equivalent of substituted benzamide.

6. A manufacturing method for N-alkoxymethyl benzamide derivatives in accordance with claim 3, wherein said acid catalyst comprises a cation exchanging resin.

7. A manufacturing method for N-alkoxymethyl benzamide derivatives in accordance with any one of claims 2 or 3, wherein said mixing procedure and said separation procedure are conducted continuously.

* * * * *